(12) United States Patent
Desai et al.

(10) Patent No.: US 11,938,213 B2
(45) Date of Patent: Mar. 26, 2024

(54) HAIR COSMETIC COMPOSITIONS CONTAINING CATIONIC POLYMERS, ACRYLATE-BASED POLYMERS, GUMS, AND POLYOLS

(71) Applicant: L'Oreal, Paris (FR)

(72) Inventors: Prashansa Mayank Desai, Hoboken, NJ (US); Aziza Khader Suleiman, Paterson, NJ (US); Vanessa Decarlo, Roselle Park, NJ (US)

(73) Assignee: L'OREAL, Paris (FR)

( * ) Notice: Subject to any disclaimer, the term of this patent is extended or adjusted under 35 U.S.C. 154(b) by 469 days.

(21) Appl. No.: 16/587,384

(22) Filed: Sep. 30, 2019

(65) Prior Publication Data

US 2021/0093541 A1    Apr. 1, 2021

(51) Int. Cl.
| | | |
|---|---|---|
| A61K 8/73 | (2006.01) | |
| A61K 8/34 | (2006.01) | |
| A61K 8/81 | (2006.01) | |
| A61Q 5/06 | (2006.01) | |
| A61Q 5/12 | (2006.01) | |

(52) U.S. Cl.
CPC .............. *A61K 8/731* (2013.01); *A61K 8/345* (2013.01); *A61K 8/737* (2013.01); *A61K 8/8152* (2013.01); *A61K 8/8182* (2013.01); *A61Q 5/06* (2013.01); *A61Q 5/12* (2013.01); *A61K 2800/5422* (2013.01); *A61K 2800/5426* (2013.01)

(58) Field of Classification Search
None
See application file for complete search history.

(56) References Cited

U.S. PATENT DOCUMENTS

| | | | | |
|---|---|---|---|---|
| 5,679,328 A | * | 10/1997 | Dupuis | ................. A61Q 5/006 424/70.13 |
| 9,072,683 B2 | | 7/2015 | Cao et al. | |
| 2006/0134049 A1 | | 6/2006 | Keenan et al. | |
| 2012/0289590 A1 | * | 11/2012 | Ritterman | ............... A61P 17/10 514/458 |
| 2013/0164244 A1 | * | 6/2013 | Molenda | .................. A61K 8/73 424/70.9 |

FOREIGN PATENT DOCUMENTS

| | | |
|---|---|---|
| KR | 100834681 | 6/2008 |
| WO | 2009/007339 A2 | 1/2009 |
| WO | 2019/048193 A1 | 3/2019 |

OTHER PUBLICATIONS

International Search Report and Written Opinion dated Dec. 18, 2020 for corresponding PCT Application No. PCT/US2020/053033.

* cited by examiner

*Primary Examiner* — Nicole P Babson
(74) *Attorney, Agent, or Firm* — POLSINELLI PC

(57) ABSTRACT

The instant disclosure relates to hair cosmetic compositions that impart desirable cosmetic properties to hair, in particular, curly hair. The hair cosmetic compositions typically include a nonionic gum, a cationic guar gum, a cationic cellulosic quaternary ammonium compound, an acrylate-based polymer, a polyol and water.

14 Claims, No Drawings

HAIR COSMETIC COMPOSITIONS CONTAINING CATIONIC POLYMERS, ACRYLATE-BASED POLYMERS, GUMS, AND POLYOLS

FIELD OF THE DISCLOSURE

The instant disclosure relates to hair cosmetic compositions that are particularly useful for improving the quality of hair, in particular, curly hair, and which can impart beneficial properties such as styling/shaping, curl definition, frizz control, retention of shape/curl, curl pick up, discipline as well as hydration, moisture, and smoothness. Also disclosed are methods for using the hair cosmetic compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades, which m requires the use of oxidizing agents.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, different types of hair styling products have been developed by manufacturers that are aimed to help consumers achieve a desired look, including one or more of fuller hair, thicker hair, sleek and straight hair, frizz-free hair, and defined curls. These products are typically provided in forms that are applied after the shampooing and conditioning processes are completed.

In one example, styling products are available that provide protection against external factors such as protection from moisture to minimize or reduce frizziness. To achieve this benefit, a water-resistant film or coating may be applied to the hair using film-forming polymers. Depending on the chemical make-up of the film-forming polymers. Product formulations that include these polymers can tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

In one example, styling products are available that provide protection against external factors such as protection from moisture to minimize or reduce frizziness. To achieve this benefit, a water-resistant film or coating may be applied to the hair using film-forming polymers. Depending on the chemical make-up of the film-forming polymers. Product formulations that include these polymers can tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or sticky feeling and/or too much "crunch" (i.e. the films become hard and brittle and therefore have a crunchy feel or sound when manipulated), which is undesirable to many consumers.

Increasingly, consumers also seek hair products that have a natural look and feel, a light-weight feel, while imparting good styling benefits to hair. Further, consumers seek products that offer multiple benefits, for example, combining frizz reduction and style hold with softening, elongation or lengthening effects while still providing good curl definition. Moreover, consumers desire hair products that can protect hair from extreme environmental conditions such as high humidity which causes the hair to become very frizzy, unmanageable, and lose its shape and style.

One important functional element of such products is their ability to style the hair without weighing it down. Many consumers seek hair products which have excellent style memory, cosmeticity, and shine without heavily coating the hair strands, and thereby weighing the hair down. The resulting feel and texture of the hair after the application are important elements of such commodities. While different technologies and products exist in the market for hair styling products, there is still a need for improvement in these areas as well as the need to provide caring benefits that are not typically found in a styling product.

Thus, the object of this invention is related to a composition and method of treating hair utilizing hair compositions which will deliver both caring and styling/shaping benefits to hair such as frizz control, discipline, control/hold, softness, smoothness, shine, natural feel, and hydration, but will not result in any product build up or leave the hair feeling heavily coated or weighed down, stiff, or brittle.

The object of the invention is also to deliver all other styling benefits that curly haired consumers desire on a daily basis: curl definition, moisture, conditioning, hold, frizz control, curl/shape retention, curl pick up, moisture to curls, and not leaving the curls feeling greasy or stiff. The composition from such an invention can be applied on wet or damp hair using a "wash and go" or "twist out" method. "Wash and go" involves applying the product, section by section, to wet or damp hair and letting it air dry. The "twist out" method involves manipulating the curl pattern in order to provide elongation or lengthening while maintaining other styling benefits. It can be done by applying the product on wet hair and twisting small sections of the hair and letting it air dry.

The object of the invention is also to provide these attributes that will last even when hair is exposed to high humidity conditions. The invention is particularly useful for treating and providing the described properties to curly hair (of varying degrees of curl) and to wavy hair.

SUMMARY OF THE DISCLOSURE

It has surprisingly been found that compositions and methods of treating hair according to the present invention impart styling/shaping, curl definition, curl retention, curl pick up, frizz control, volume control, control/hold, discipline, hydration, moisture, and smoothness and other cosmetic benefits to the hair, while still providing a light weight feel and a clean feel (non-greasy, non-oily) to the hair.

One aspect of the invention pertains to a hair cosmetic composition comprising:
(a) at least one nonionic gum;
(b) at least one cationic guar gum;
(c) at least one cationic cellulosic quaternary ammonium compound;
(d) at least one polymer chosen from an acrylate-based polymer, VP/VA copolymer, and a mixture thereof;
(e) at least one polyol chosen from ethylene glycol, propylene glycol, butylene glycol, hexylene glycol, pentylene glycol, diethylene glycol, dipropylene glycol, 1,3 propanediol, polyethylene glycols, caprylyl glycol, diglycerin, glycerin, and a mixture thereof and present in an amount of at least 0.5 wt. %, based on the total weight of the hair cosmetic composition; and
(f) water;
wherein the weight ratio of the cationic guar gum to the nonionic gum is less than 1.

Another aspect of the invention pertains to methods of treating hair. In some embodiments, the method comprises applying any of the compositions described herein to hair. In one or more embodiments, the composition is applied to hair as part of a hair styling/shaping or caring routine. In some embodiments, the composition is applied after treating the hair with a shampoo and/or conditioner.

DETAILED DESCRIPTION OF THE DISCLOSURE

The term "hair cosmetic composition" encompasses many types of compositions for application to the hair, for example, hair lotions, hair creams, hair gel creams, hair conditioners, hair masques (masks), etc, which can be used either as leave-on or rinse-off treatments or products. A hair cosmetic composition according to the invention is characterized by its ability to provide a cosmetic (such as styling/shaping and caring) benefit to the hair. Non-limiting examples of benefits that can be imparted by the compositions of the present invention to hair include frizz control, curl definition, curl retention, curl pick-up, styling/shaping, discipline, frizz control, hold/control, manageability, smoothness, softness, suppleness, hydration (does not feel dry) and natural feel.

The hair cosmetic compositions of the instant disclosure typically include:
(a) at least one nonionic gum;
(b) at least one cationic guar gum;
(c) at least one cationic cellulosic quaternary ammonium compound;
(d) at least one polymer chosen from an acrylate-based polymer, VP/VA copolymer, and a mixture thereof;
(e) at least one polyol chosen from ethylene glycol, propylene glycol, butylene glycol, hexylene glycol, pentylene glycol, diethylene glycol, dipropylene glycol, 1,3 propanediol, polyethylene glycols, caprylyl glycol, diglycerin, glycerin, and a mixture thereof and present in an amount of at least 0.5 wt. %, based on the total weight of the hair cosmetic composition; and
(f) water;
wherein the weight ratio of the cationic guar gum to the nonionic gum is less than 1.

In one embodiment, the at least one nonionic gum includes hydroxypropyl guar.

In one embodiment, the at least one nonionic gum is present in an amount of about 0.01 to about 10 wt. %, about 0.1 to about 8 wt. %, about 0.2 to about 8 wt. %, about 0.3 to about 7 wt. %, about 0.4 to about 6 wt. %, about 0.5 to about 5 wt. %, about 1 to about 4 wt. %, or about 1.2 to about 3 wt. %, based on the total weight of the hair cosmetic composition.

In one embodiment, the at least one cationic guar gum is hydroxypropyl guar hydroxypropyltrimonium chloride.

In one embodiment, the at least one cationic guar gum is present in an amount of about 0.01 to about 2 wt. %, about 0.1 to about 1.8 wt. %, about 0.12 to about 1.5 wt. %, about 0.15 to about 1 wt. %, or about 0.2 to about 0.5 wt. %, based on the total weight of the hair cosmetic composition In one embodiment, the at least one cationic cellulosic quaternary ammonium compound is selected from a copolymer of hydroxyethyl cellulose and of diallyldimethylammonium chloride.

In an embodiment, the at least one cationic cellulosic quaternary ammonium compound is polyquaternium-4.

In an embodiment, the at least one cationic cellulosic quaternary ammonium compound comprises polyquaternium-4 and a second cationic cellulosic quaternary ammonium compound.

In an embodiment, the at least one cationic cellulosic quaternary ammonium compound is present in an amount of about 0.01 to about 5 wt. %, or about 0.1 to about 4 wt. %, or about 0.15 to about 3 wt. %, or about 0.2 to about 2 wt. %, based on the total weight of the hair cosmetic composition In an embodiment, the at least one polymer chosen from an acrylate-based polymer, VP/VA copolymer, and a mixture thereof is selected from VP/dimethylamino ethylmethacrylate copolymer, VP/VA copolymer, and a mixture thereof.

In an embodiment, the at least one polymer chosen from an acrylate-based polymer, VP/VA copolymer, and a mixture thereof is present in an amount of about 0.01 to about wt. %, about 0.5 to about 8 wt. %, about 1 to about 6 wt. %, or about 1.5 to about 4 wt. %, based on the total weight of the hair cosmetic composition.

In an embodiment, the at least one polyol is selected from butylene glycol, propylene glycol, dipropylene glycol, caprylyl glycol, glycerin, and a mixture thereof.

In an embodiment, the at least one polyol is selected butylene glycol, propylene glycol, glycerin, and a mixture thereof.

In an embodiment, the at least one polyol is selected butylene glycol, dipropylene glycol, and a mixture thereof.

In an embodiment, the at least one polyol is butylene glycol.

In an embodiment, the at least one polyol is dipropylene glycol.

In an embodiment, the at least one polyol is propylene glycol.

In an embodiment, the at least one polyol is glycerin.

In an embodiment, the at least one polyol is present in an amount of about 0.5 to about 15 wt. %, about 1 to about 14 wt. %, about 1.5 to about 12 wt. %, about 2 to about wt. %, about 2.5 to about 9 wt. %, about 3 to about 8.5 wt. %, about 3.5 to about 8 wt. %, about 4 to about 7 wt. %, based on the total weight of the hair cosmetic composition.

In an embodiment, the compositions of the present invention is substantially free or is free of silicones, In an embodiment, the compositions of the present invention is substantially free or is free of non-ester oils such as mineral oil.

In embodiment, the hair cosmetic composition of the present invention comprises:
- (a) at least one nonionic gum comprising hydroxypropyl guar present in an amount of 1 to about 4 wt. %, or about 1.2 to about 3 wt. %, based on the total weight of the hair cosmetic composition;
- (b) at least one cationic guar gum comprising hydroxypropyl guar hydroxypropyltrimonium chloride present in an amount of about 0.15 to about 1 wt. %, or about 0.2 to about 0.5 wt. %, based on the total weight of the hair cosmetic composition;
- (c) at least one cationic cellulosic quaternary ammonium compound selected from polyquaternium-4 and present in an amount of about 0.15 to about 3 wt. %, or about 0.2 to about 2 wt. %, based on the total weight of the hair cosmetic composition;
- (d) at least one polymer chosen from an acrylate-based polymer, VP/VA copolymer, and a mixture thereof selected from VP/dimethylamino ethylmethacrylate copolymer, VP/VA copolymer, and a mixture thereof, and present in an amount of about 1 to about 6 wt. %, or about 1.5 to about 4 wt. %, based on the total weight of the hair cosmetic composition;
- (e) at least one polyol chosen from butylene glycol, propylene glycol dipropylene glycol, glycerin, and a mixture thereof and present in an amount of about 3.5 to about 8 wt. %, or about 4 to about 7 wt. %, based on the total weight of the hair cosmetic composition; and
- (f) water;

wherein the weight ratio of the cationic guar gum to the nonionic gum is from about 0.01 to about 0.9, or about 0.1 to about 0.5, or about 0.12 to about 0.3, including ranges and sub-ranges there between, or such as at about 0.01, 0.05, 0.1, 0.12, 0.125, 0.13, 0.135, 0.15, 0.17, 0.2, 0.225, 0.25, or 0.3.

In an embodiment, the at least one polymer chosen from an acrylate-based polymer, VP/VA copolymer, and a mixture thereof is VP/dimethylamino ethylmethacrylate copolymer.

In an embodiment, the at least one polymer chosen from an acrylate-based polymer, VP/VA copolymer, and a mixture thereof is VP/VA copolymer.

The present invention also relates to a method of treating hair, the method comprising applying any one of the above-described compositions of the invention to hair. Said method comprises providing to hair one or more of: shaping or styling benefits;
curl definition;
curl retention;
long-lasting curl definition;
humidity-resistant curl definition;
frizz control;
styling/shaping hold;
long lasting or durable styling/shaping hold;
smoothness;
softness;
natural feel;
hydration;
light-weight feel; or
shine.

The above compositions, which feature a unique combinations of ingredients, advantageously provide frizz control, curl definition, curl retention, curl pick-up, discipline, hold/control, styling/shaping, long lasting or humidity-resistant styling and curl care benefits together with natural feel, light-weight feel, softness, and smoothness.

The hair cosmetic compositions described herein may be in any suitable physical form. Suitable forms include, but are not limited to low to moderate viscosity liquids, lotions, milks, gel creams, creams, pastes, clays, conditioners, masks, and the like.

The hair cosmetic compositions may be packaged in a variety of different containers, such as, for example, a ready-to-use container. Non-limiting examples of useful packaging include tubes, jars, caps, unit dose packages, and bottles, including squeezable tubes and bottles and spray bottles.

Nonionic Gums

The nonionic gum of the compositions of the present invention is selected from nonionic guar gums, including hydroxypropyl guar gum. Hydroxypropyl guar gum may be commercially available under the tradename JAGUAR HP 8, from the company Rhodia.

The total amount of the nonionic gum in the composition, if present, may vary but is typically from about 0.01 to about 10 wt. %, based on the total weight of the composition. In some instances, the total amount of nonionic gum (s) is from about 0.1 to about 8 wt. %, about 0.2 to about 8 wt. %, about 0.3 to about 7 wt. %, about 0.4 to about 6 wt. %, about 0.5 to about 5 wt. %, about 1 to about 4 wt. %, or about 1.2 to about 3 wt. %, based on the total weight of the composition, including ranges and sub-ranges there between.

Thus, the nonionic gum is present, by weight, based on the total weight of the composition, in an amount from about 0.01, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, to about 10 wt. %, including increments and ranges therein and there between.

Cationic Guar Gum

The cationic guar gum of the compositions of the present invention is preferably hydroxypropyl guar hydroxypropyltrimonium chloride, typically commercially available under the tradename of JAGUAR C 162, from the company Rhodia.

The total amount of the at least one cationic guar gum in the composition, if present, may vary but is typically from about 0.01 to about 2 wt. %, about 0.1 to about 1.8 wt. %, about 0.12 to about 1.5 wt. %, about 0.15 to about 1 wt. %, or about 0.2 to about 0.5 wt. %, based on the total weight of the hair cosmetic composition.

In some embodiments, the total amount of the at least one cationic guar gum is from about 0.01, 0.05, 0.075, 0.1, 0.125, 0.15, 0.175, 0.2, 0.225, 0.25, 0.275, 0.3, 0.325, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, to about 2 wt. %, based on the total weight of the hair cosmetic composition.

Cationic Cellulosic Quaternary Ammonium Compound

Non-limiting examples of cationic cellulosic quaternary ammonium compounds include cationic polymers such as a copolymer of hydroxyethyl cellulose and of diallyldimethylammonium chloride (Polyquaternium-4).

In an embodiment, the cationic cellulosic quaternary ammonium compound of the present invention is polyquaternium-4, which is commercially available under the tradename CELQUAT LOR from the company Akzo Nobel.

The total amount of the at least one cationic cellulosic quaternary ammonium compound may vary, but in some cases, the total amount is about 0.01 to about 5 wt. %, based on the total weight of the hair cosmetic composition. In some cases, the total amount of the at least one cationic cellulosic quaternary ammonium compound is about to about 4 wt. %, about 0.15 to about 3 wt. %, about 0.2 to about 2 wt. %, based on the total weight of the hair cosmetic composition, including ranges and sub-ranges there between.

In some embodiments, the total amount of the at least one cationic cellulosic quaternary ammonium compound is from about 0.01, 0.05, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.6, 0.625, 0.65, 0.675, 0.7, 0.725, 0.75, 0.775, 0.8, 0.825, 0.85, 0.875, 0.9, 0.925, 0.975, 1, 1.5, 2, 2.5, 3, 3.5, to about 5 wt. %, based on the total weight of the hair cosmetic composition.

Acrylate-Based Polymer and VP/VA Copolymer

The at least one polymer chosen from an acrylate-based polymer, VP/VA copolymer, and a mixture thereof may be selected from homopolymers and copolymers derived from acrylic or methacrylic esters or amides, examples of which are: copolymers of acrylamide and of dimethylaminoethyl acrylate quaternized with dimethyl sulfate or with a dimethyl halide, such as the product sold under the name HERCOFLOC by the company Hercules; the copolymers of acrylamide and of methacryloyloxyethyltrimethylammonium chloride and sold under the name BINA QUAT P 100 by the company Ciba Geigy; the copolymer of acrylamide and of methacryloyloxyethyltrimethylammonium methosulfate sold under the name RETEN by the company Hercules; quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755 or GAFQUAT 755N (e.g., polyquaternium-11), or alternatively the products known as COPOLYMER 845, 958 and 937 (e.g., VP/dimethylamino ethylmethacrylate copolymer), dimethylaminoethyl acrylate/vinylcaprolactam/vinylpyrrolidone terpolymers, such as the product sold under the name GAFFIX VC 713 by the company ISP or the product sold under the name Gafquat HS-100 by the company ISP; vinylpyrrolidone/methacrylamidopropyldimethylamine copolymers sold, for example, under the name STYLEZE CC 10 by ISP; quaternized vinylpyrrolidone/dimethylaminopropylmethacrylamide copolymers such as the product sold under the name GAFQUAT HS 100 by the company ISP, and crosslinked polymers of methacryloyloxy($C_1$-$C_4$) alkyltri($C_1$-$C_4$)alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide.

In preferred embodiments, the at least one polymer chosen from an acrylate-based polymer, VP/VA copolymer, and a mixture thereof is selected from VP/dimethylamino ethylmethacrylate copolymer, VP/VA copolymer, and a mixture thereof.

In an embodiment, the at least one polymer chosen from an acrylate-based polymer, VP/VA copolymer, and a mixture thereof is VP/dimethylamino ethylmethacrylate copolymer, commercially available under the tradename, COPOLYMER 845-O from the company ISP Ashland.

In an embodiment, the at least one polymer chosen from an acrylate-based polymer, VP/VA copolymer, and a mixture thereof is VP/VA polymer, commercially available under the tradename, PVP/VA W 735 from the company ISP Ashland, or under the tradename LUVISKOL VA 73 W from the company BASF.

The total amount of the at least one polymer chosen from an acrylate-based polymer, VP/VA copolymer, and a mixture thereof may vary, but in some cases, the total amount is about 0.01 to about 10 wt. %, based on the total weight of the hair cosmetic composition. In some cases, the total amount of the at least one polymer chosen from an acrylate-based polymer, VP/VA copolymer, and a mixture thereof is about 0.5 to about 8 wt. %, about 1 to about 6 wt. %, or about 1.2 to about 4 wt. %, or about 1.4 to about 3 wt. %, or about 1.5 to about 2.5 wt. %, based on the total weight of the hair cosmetic composition, including ranges and sub-ranges there between.

In some embodiments, the at least one polymer chosen from an acrylate-based polymer, VP/VA copolymer, and a mixture thereof is from about 0.01, 0.05, 0.1, 0.125, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.9, 0.925, 0.95, 0.975, 1, 1.5, 2, 2.5, 3, 3.5, 4, 4.5, 5, to about 10 wt. %, based on the total weight of the hair cosmetic composition, including ranges and sub-ranges there between.

Polyols

The term "polyol" should be understood as meaning, within the meaning of the present disclosure, an organic molecule comprising at least two free hydroxyl groups. The polyols of the cosmetic composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the compositions of the present disclosure, in certain instances, include from ethylene glycol, propylene glycol, butylene glycol, hexylene glycol, pentylene glycol, diethylene glycol, dipropylene glycol, 1,3 propanediol, polyethylene glycols, caprylyl glycol, diglycerin, glycerin, or mixtures thereof. In some cases, the polyol is butylene glycol. In some further cases, the at least one polyol comprises butylene glycol. Additionally, in some cases, the compositions comprise at least butylene glycol, and one or more polyols other than butylene glycol such as propylene glycol, dipropylene glycol, and/or glycerin.

Non-limiting examples of polyols that may, optionally, be included in the cosmetic include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof In one or more embodiments, the at least one polyol comprises one or more glycol compounds. In further embodiments, the glycol compounds are selected from the group consisting of hexylene glycol, butylene glycol, propylene glycol, dipropylene glycol, and combinations thereof. In other embodiments, the at least one polyol comprises butylene glycol.

In other embodiments, the at least one polyol comprises glycerin and at least one glycol selected from the group consisting of hexylene glycol, butylene glycol, propylene glycol, dipropylene glycol, glycerin, and combinations thereof.

The total amount of the at least one polyol may vary, but in some cases, the total amount is at least about 0.5 wt. %, such as from about 0.5 to about 15 wt. %, about 1 to about 14 wt. %, about 1.5 to about 12 wt. %, about 2 to about 10 wt. %, about 2.5 to about 9 wt. %, about 3 to about 8.5 wt. %, about 3.5 to about 8 wt. %, about 4 to about 7 wt. %, based on the total weight of the hair cosmetic composition, including ranges and sub-ranges there between.

In some embodiments, the total amount of the at least one polyol is from about 0.6, 0.7, 00.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 10, 10.5, 11, 11.5, 12, to about 10 wt. %, based on the total weight of the hair cosmetic composition, including ranges and sub-ranges there between.

Water

The amount of water in the hair cosmetic compositions may be at least 50 wt. %, or from about 60 to about 95 wt. %, about 70 to about 95 wt. %, about 80 to about 95 wt. %, about 85 to about 95 wt. %, based on the weight of the composition.

Organic Solvents

The hair cosmetic compositions may optionally include at least one organic solvent (non-silicone solvents) other than the polyols of the present disclosure.

Non-limiting examples of organic solvents include, for example, alcohols (for example, $C_{1-15}$, $C_{1-10}$, or $C_{1-6}$ alcohols, glycol ethers, or mixtures thereof.

Non-limiting examples of organic solvents include monoalcohols such as ethyl alcohol, isopropyl alcohol, propyl alcohol, benzyl alcohol, and phenylethyl alcohol, and glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

The total amount organic solvent(s) in the hair cosmetic composition, if present, can vary but is typically about 0.1 to about 10 wt. %, based on the total weight of the hair cosmetic composition. In some cases, the total amount of water-soluble solvent(s) is about 0.1 to about 8 wt. %, about 0.1 to about 6 wt. %, about 0.1 to about 0.5 to about 10 wt. %, about 0.5 to about 8 wt. %, about 0.5 to about 6 wt. %, about 0.5 to about 5 wt. %, about 1 wt. %, about 2 wt. %, about 3 wt. %, or about 4 wt. %, including all ranges and subranges there between.

Other Components

In one or more embodiments, the hair cosmetic compositions described herein may contain one or more additional ingredients. Examples include, but are not limited to surfactants, emulsifiers, thickeners (e.g, gums or polysaccharides other than the claimed gums), silicones, oils (natural or plant-based or synthetic), fillers, monosaccharides, di-saccharides, plant extracts, vitamins, fragrance, pH adjusters, and preservatives. Additional details regarding such additional ingredients follows below.

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

In an embodiment, the compositions of the present disclosure are in the form of a leave-on product such as a styling/shaping product, leave-on product for curly hair (such as combing creams or combing gels or combing lotions), anti-frizz hair product, or rinse-off or leave-on mask product.

In an embodiment, the compositions of the present disclosure are in the form of a rinse-off cream product such as a mask product.

In an embodiment, the compositions of the present disclosure are in the form of a leave-on cream product such as a styling/shaping product.

In an embodiment, the compositions of the present disclosure are in the form of a leave-on cream product such as a styling/shaping and/or conditioning product.

In an embodiment, the compositions of the present disclosure are in the form of a leave-on or a rinse-off styling conditioner.

In an embodiment, the compositions of the present disclosure are in the form of an emulsion such as an oil-in-water emulsion or a water-in-oil emulsion.

Methods

Another aspect of the invention pertains to methods of using the hair cosmetic compositions described herein. The methods generally comprise applying any of the hair cosmetic compositions described to hair. The hair cosmetic compositions may be useful in a variety of settings, and either for chemically treated or untreated hair. Use on treated hair can include chemically relaxed/straightened hair or chemically dyed or bleached or lightened/highlighted hair. Use on hair may include as part of a shampoo, part of a conditioner or as a conditioner, as a pre-treatment, or after cleansing or conditioning or washing the hair as a leave-on treatment for styling/shaping the hair or caring for curly hair or as a leave-on or rinse-off mask treatment.

Methods of treating hair according to the disclosure may include applying a hair cosmetic composition of the instant disclosure to the hair (wet, damp, or dry hair), allowing the hair treatment to remain on the hair for a sufficient amount of time, and rinsing the hair cosmetic composition from the hair or allowing the hair treatment to be left on the hair as a leave-on product. The hair cosmetic composition may be applied to the hair before, during, or after other hair cosmetic compositions (e.g., a shampoo, a conditioner, a mask, a cream, a lotion, a gel, etc.).

Other methods of treating hair according to the disclosure involve a wash and go/braiding technique. Typically, the hair type on which this method is used is curly hair.

Other methods of treating hair according to the disclosure involve a twist out technique. Typically, the hair type on which this method is used is curly hair.

The hair cosmetic composition may be allowed to remain on the hair for a period of time, for example from about a few seconds (1, 3, 5, or 10 seconds) to about 10, 20, or 30 minutes, or longer.

The hair cosmetic compositions may be useful for treating chemically treated hair.

Described above is the individual application of a hair cosmetic composition or the combined or layered application of a hair cosmetic composition with another composition. In some cases, a hair cosmetic composition is individually applied to the hair and also combined or layered with another composition that is also applied to the hair.

Kits

The hair cosmetic compositions of the instant disclosure may be incorporated into a kit. For example, the kits may include at least one hair cosmetic composition according to the instant disclosure. The kits may also include one or more hair cosmetic compositions (according the instant disclosure), a shampoo and/or a conditioner and/or a mask.

Implementation of the present disclosure is provided by way of the following examples. The examples serve to illustrate the technology without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced having the ingredients as listed in the tables below. The balance of all formulas was water.

Example I: Compositions

TABLE 1A

Formulations

| INGREDIENT | | Invention Formulas | | Comparative Formulas | | | | |
|---|---|---|---|---|---|---|---|---|
| TYPE | US INCI INGRDIENT NAME | A | B | C | D | E | F | G |
| Gums and other polysaccharides | HYDROXYPROPYL GUAR (Nonionic) | 1.6 | 1.5 | — | 1.7 | 1.7 | 0.3 | 0.3 |
| | HYDROXYPROPYL GUAR HYDROXYPROPYLTRIMONIUM CHLORIDE (Cationic) | 0.2 | 0.2 | — | — | — | — | — |
| | XANTHAN GUM | — | — | — | — | — | 3 | — |
| | ACACIA SENEGAL GUM | — | — | — | — | — | — | 0.01 |
| | DEHYDROXANTHAN GUM | — | — | — | 0.1 | — | — | 1 |
| | PECTIN | — | — | — | — | — | 0.4 | 0.4 |
| Quaternary Ammonium Compound | POLYQUATERNIUM-4 (Cationic Cellulosic Polymer) | 0.7 | 0.8 | 0.3 | 0.8 | 0.8 | — | — |
| | CETRIMONIUM CHLORIDE (Cationic surfactant; non-polymeric) | — | — | 0.3 | — | — | — | — |
| Polymer | VP/DIMETHYLAMINOETHYLMETHACRYLATE COPOLYMER (Cationic Acrylate-based) | 1-2 | — | 0.1 | — | — | — | — |
| | VP/VA COPOLYMER (Nonionic) | — | 1-2 | — | 1.7 | 1.7 | — | — |
| | PVP (Nonionic) | — | — | 2 | — | — | — | — |
| Polyol | BUTYLENE GLYCOL AND/OR PROPYLENE GLYCOL AND/OR DIPROPYLENE GLYCOL AND/OR GLYCERIN | 4 | 6.5 | 4 | — | — | 5 | 5 |
| Silicone | PEG/PPG-22/24 DIMETHICONE | — | — | 0.5 | — | — | — | — |
| Additives - fillers, sugars, oils, plant/fruit extracts, fragrance, pH adjusters, Vitamins | CALCIUM CARBONATE AND HYDROGENATED STARCH HYDROLYSATE | — | — | — | — | — | 11.0 | 11.0 |
| | GLUCOSE AND/OR SUCROSE | — | — | — | — | — | 2 | 2 |
| | PEG-40 HYDROGENATED CASTOR OIL | 0.3 | 0.4 | 0.9 | 0.2 | 0.2 | — | — |
| | ONE OR MORE OF FRAGRANCE, CITRIC ACID, TOCOPHEROL, PLANT AND/OR FRUIT EXTRACT, PLANT/VEGETABLE OILS | <1 | <1 | <1 | <1 | <1 | <1 | <1 |
| Preservative | PRESERVATIVE(S) | <2 | <2 | <2 | <2 | <2 | <2 | <2 |
| Organic Solvent | C2 TO C22 MONOALCOHOLS | <2 | <2 | <2 | <2 | <2 | <2 | <2 |
| Solvent | WATER | QS 100 | QS 100 | QS 100 | QS 100 | QS 100 | QS 100 | QS 100 |

Process of making the invention composition: The inventive formula was prepared according to the following procedure:
1. Add water to suitably sized beaker. Sprinkle in PQ-4. Heat to 60-65C with mixing. Mix until uniform.
2. Cool batch to 40-45C, add guar and cationic guar. Mix until uniform.
3. To the main batch at 40-45C, add following ingredients one at a time mixing well between each addition: polymer, glycol and preservatives.
4. Cool batch down to room temperature.
5. In a side beaker premelt fragrance solubilizer at 40-45C. Once completely liquefied, add fragrance and mix until clear and uniform. Add to main batch. Mix until uniform.
6. Add citric acid to adjust pH 5.3 and mix until uniform.

TABLE 1B

Observations and cosmetic performance

| Formulas from TABLE 1A | Cosmetic performance or effect on hair |
|---|---|
| A | Soft, conditioning, holds curls, long lasting |
| B | Soft, conditioning, higher hold for more texturized hair |
| C | Not very slippery to touch, not as conditioning |
| D | Conditioning but very wetting, still soapy, crunchy |
| E | Sticky to touch, soapy on hair, crunchy |
| F | Hair feels dry on application, not slippery due to lack of PQ-4; crunchy (similar to brittleness) |
| G | Non flowy texture results to uneven application; not as conditioning because does not contain cationic guar; crunchy |

Table 1B above shows that the Inventive formulas A and B imparted to hair the cosmetic attribute of softness, conditioning, curl hold or higher (greater) hold, and long lasting benefits. On the other hand, some of the Comparative formulas (C and G) were not as conditioning. Hair treated with Comparative formula C did not have enough slip and hair treated with Comparative formula G felt crunchy, an effect that may be associated with a feeling of brittleness or a coating on that breaks when the hand is passed through the hair. Hair treated with Comparative formula F felt dry to the touch, did not have enough slip and was crunchy. Hair treated with Comparative formula E felt sticky and soapy and was crunchy. Hair treated with Comparative formula F felt conditioned but it felt soapy and wet. Thus, the Inventive formulas showed the best balance between softness/conditioning and hold without imparting a crunchy feel to the hair. In addition, the inventive formulas did not impart a sticky or soapy effect on the hair.

Example II Tests to Show the Contribution of Various Ingredients in the Inventive Compositions The formulas/compositions of the invention can be considered to be a hybrid technology that relies on a combination of different cationic materials to achieve the most commonly desired attributes amongst people with curly hair such as smoothness and moisture without losing control and hold without the crunchy feel.

Tables 2A and 2B below depict the assessed hold and moisture on the hair on heads of human volunteers treated with different combinations of various ingredients using the general composition of Formula A as the base formula for making the formulas for the tests. The test formulas were applied as leave on products on the hair, i.e., the hair was not washed or rinsed with water. Table 3 shows a summary of the information in Tables 2A and 2B based on how each of the material used in the selected combination contributed to different attributes including moisture and hold. The assessments were made by salon hair dressers.

The salon hair dressers also used different techniques to assess the product performance. The test formulas were air dried on some models and manipulation techniques like finger coils, 2 strand technique, lacer technique were performed on the hair of some models. Various techniques were employed as some people with very texturized hair used these protective hair techniques so the performance of the invention was also confirmed using these various techniques. Finger coils is when the stylists apply the product to wet hair that is sectioned and coil the hair in each section with their fingers and let it dry to achieve more defined curls. 2 strand technique is a protective hair style used by people with highly texturized hair. In this technique, the stylist sections the hair and makes braids using 2 strands of each section resulting in multiple braids. Lacer technique is similar to 2 strand braiding but it uses a foam strip along with the hair in each section. This technique is used to create more defined curls.

One or more of the following benefits to hair were observed when hair was treated with the inventive formulas:

Moisturizing, softness, hold was moveable.

Can be used on all curl types—tight curls need more product while less tight or looser curls need less product.

Hold, shine and slip.

Good hold.

Once dry, the hair is not matte and product does not flake.

Has good shine.

Hair exhibited a little bit of positive crunch.

Less drying time, better slip and hold.

TABLE 2A

HOLD

|  | Cationic Guar | Polymer (VP/dimethyl-amino ethylmethacrylate copolymer) | Combination |
|---|---|---|---|
| Control | ✓ | x | ✓ |
| Curl Definition | ✓ | ✓ | ✓ |
| Frizz/Static Control | ✓ | x | ✓ |
| Long Lasting | x | ✓ | ✓ |
| Curl Regularity | x | ✓ | ✓ |

Table 2A shows that when only cationic guar was present, the composition imparted control, curl definition and frizz control to hair but did not impart long lasting hold or curl regularity. When only VP/dimethylamino ethylmethacrylate copolymer was present, the composition imparted curl definition long lasting hold, and curl regularity. When both were present, all desired hold attributes were present.

TABLE 2B

MOISTURE

|  | Guar | Quaternary Ammonium Compound (Polyquaternium-4) | Combination |
|---|---|---|---|
| Smooth | ✓ | ✓ | ✓ |
| Soft | ✓ | x | ✓ |

TABLE 2B-continued

MOISTURE

|  | Guar | Quaternary Ammonium Compound (Polyquaternium-4) | Combination |
|---|---|---|---|
| Slip | x | ✓ | ✓ |
| Bounce | x | ✓ | ✓ |
| Flexible | ✓ | x | ✓ |

Table 2B shows that when only guar was present, the composition imparted smoothness, softness, and flexibility to hair but did not impart slip or bounce. When only polyquaternium-4 was present, the composition imparted smoothness, slip, and bounce. When both were present, all desired hold attributes were present.

TABLE 3

Ingredients/Combinations

|  | Guar | Cationic Guar | Polymer (VP/dimethylamino ethylmethacrylate copolymer) | Quaternary Ammonium Compound (Polyquaternium-4) | Final Formula (Invention) |
|---|---|---|---|---|---|
| Control | ✓ | x | x | x | ✓ |
| High Hold | x | x | ✓ | x | ✓ |
| Smooth | x | ✓ | x | ✓ | ✓ |
| Slip | x | x | x | ✓ | ✓ |
| Frizz Control | x | ✓ | x | x | ✓ |
| Curl Definition | x | ✓ | ✓ | x | ✓ |
| Soft | ✓ | x | x | x | ✓ |
| Flexible | ✓ | x | x | x | ✓ |
| Moisture | ✓ | x | x | x | ✓ |

Table 3 shows a summary of Tables 2A and 2B. When all four ingredients were present, all desired hold attributes were present.

Example III Tests to Show the Contribution of the Combination of the Guar Ingredients in the Inventive Compositions Experiments conducted with different materials led the inventors to employ a combination of guar and cationic guar using the general composition of Formula A as the base formula for making the various formulas for the tests. The use of cationic guar provided the benefit of smoothness and frizz reduction. Guar was used for hold and as a viscosity modifier, giving the product the consistency it needed for ease of application. The correct ratio of the guars was discovered in order to achieve the right balance between moisture and hold in a product. Different experiments were conducted to determine the correct ratio of these guars. The ratio of the two guars was also based on sustainability scoring and performance. So various trials were made to determine the exact ratio that gives the best performance. The ratio of the 2 guars works out the best at the weight ratio of 1:8 of the cationic guar to guar.

In addition, replacing cationic guar with xanthan gum resulted in inferior performance. The use of xanthan gum made the formula too wetting and soapy. On the other hand, the guars provided good hold and smoothness. The table below depicts the results of experiments done to pick the best gums.

TABLE 4

Testing Various Guars

| Attributes/ Materials | Guar | Cationic Guar | Xanthan Gum | Cellulose Gum |
|---|---|---|---|---|
| Light hold | High | Low | Low | None |
| Definition | Medium | Low | None | Low |
| Tack | Low | Low | None | High |
| Smooth/Slip | Low | High | Medium | None |
| Frizz Reduction | None | High | Medium | Low |
| Soapy | None | Low | High | None |
| Wetting | Medium | Low | High | Low |
| Viscosity | Medium | Low | High | Low |

From the above results it is very evident that the guars provided better attributes as compared to Xanthan Gum and Cellulose Gum.

A. Salon Test—Testing Different Gum Combinations

In a salon test, Comparative Formula D which contains guar, PQ-4, VP/VA copolymer, and dehydroxanthan gum was tested against another comparative, a commercial product benchmark. The commercial benchmark contained: Water, Horsetail, Chamomile, Nettle, Marshmallow, Aloe Vera Juice, Plant Extract, Vitamin, Pectin, Preservative(s), and Fragrance.

Formula D did not contain a cationic guar. The commercial product is a gel that the manufacturer claims to provide good curl definition and length. The two formulas were tested on hair on the head of human volunteers in a half head study. Each product was applied on the hair on each half of the head (left and right sides) and the hair was assessed. The treated hair on some of the volunteers were also deconstructed (unbraided or loosened) and assessed.

The first observation during application of the products showed that the Formula D on the left side was easy to apply and had some detangling properties but it was also very wetting and soapy on the hair. The comparative commercial product, which was applied to the right side of the head was hard to distribute and more product than Formula D was required to adequately cover the hair. Upon drying, the hair treated with the comparative commercial product exhibited more clumping while the hair treated with Formula D showed even distribution. On deconstruction, the final look of the hair for each side showed that Formula D provided good curl definition, light hold, no frizz and a moisturized feel. The comparative commercial product did not provide sufficient shape control and frizz control. Deconstruction means that curls are pulled apart to create a more natural look.

From these results, it was concluded that while Formula D performed much better on hair compared to the commercial product, the use of dehydroxanthan gum made the application on hair too wetting and soapy. Also, the shaping/styling hold was not long lasting. When dehydroxanthan gum was replaced with a cationic guar, hydroxypropyl guar hydroxypropyltrimonium chloride, the resulting formula did not have a wetting and soapy effect during application on hair.

B. Salon Test

In another salon test, the inventive formula A was tested on curly hair. It was observed that the invention provided instant curls and curl definition, a good level of hold and control, long lasting performance (over two days), frizz control, shine, and does not leave hair crunchy.

Formulas A and B were also tested against the comparative, commercial product benchmark on hair on the head of human volunteers in a half head study. Each product was applied on the hair on each half of the head (left and right sides) and the hair was assessed. The treated hair was also deconstructed (unbraided or loosened) and assessed The test shows that inventive Formula A had slip and applied smoothly. On the other hand, the comparative product required more product for application and made the ends of the hair sticky. Upon deconstructing the hair, the hair treated with the invention formula had no frizz, had sealed ends, was more disciplined, had more curl definition and control and the hair looked fuller. On the other hand, the hair treated with the comparative formula was frizzy, had open ends and low control of shape.

Similar results were obtained for inventive Formula B.

Example IV Tests to Show the Contribution of Polymers in the Inventive Compositions Experiments were conducted using different polymers and different combinations of ingredients in the test formulas.

In a salon test, Formula C, a comparative formula containing PQ-4, and VP/VA copolymer was tested against another comparative, a commercial product benchmark. Formula C did not contain a hydroxypropyl guar nor a cationic guar, hydroxypropyl guar hydroxypropyltrimonium chloride. The commercial benchmark contained: Water, Horsetail, Chamomile, Nettle, Marshmallow, Aloe Vera Juice, Plant Extract, Vitamin, Pectin, Preservative(s), and Fragrance. The commercial product is a gel that the manufacturer claims to provide good curl definition and length.

Below are the results. Each product was applied on the hair on each half of the head (left and right sides).

After drying the treated hair, the hair on the right side which was treated with the comparative commercial product showed that the curls were very frizzy even though more product was required as compared to the amount of Formula C that was applied to the hair on the left side. The deconstruction of the hair showed the final look of the hair after being treated with the 2 products. The hair treated with the comparative commercial product looked frizzy and had open ends, which shows a lack of curl definition. On the other hand, the hair treated with Formula C had no frizz, had sealed ends and a more disciplined look. However, the dry hair felt crunchy which led the inventors to seek a formula that produced a more flexible and less brittle coating on hair but still provided very good shaping/styling hold.

Thus, different polymers were used to test the degree of the hold provided by the various formulas while not losing the soft smooth touch and not creating a crunchy coating on hair. Below is the table depicting the results of the polymer study. A solution was made using each polymer at 8% to create a film of the solution which was air dried before observation.

TABLE 5

Testing Various Fixing Polymers

| ATTRIBUTES/ POLYMERS | VP/dimethylamino ethylmethacrylate copolymer (Cationic) | AMP-Acrylates allyl/methacrylate copolymer(Anionic) | PVP (Nonionic) | VP/VA copolymer (Nonionic) |
|---|---|---|---|---|
| FLEXIBLE | ✓ | x | x | ✓ |
| STRETCHABLE | ✓ | x | x | x |
| BRITTLE | x | x | ✓ | x |

The above results show that VP/dimethylamino ethylmethacrylate copolymer exhibited favorable attributes for both flexibility and stretchability, thereby indicating that this polymer had the best potential to be combined with the guar gums and cationic cellulose-based compound. VP/VA copolymer also tested favorable for forming a flexible film.

Thus, in order to reduce the brittleness of the film formed by the polymer on hair, it was discovered by the inventors that the use of one or two lighter humectants, especially glycols and polyols, in the formula, helped to improve smoothness of the film and avoid flaking of the product on hair by plasticizing the film. It was thus found that the combination of polymers according to the invention produced on hair the softest film that was flexible and yet allowed the hair to hold its shape while still being very supple and free to move.

Example V Testing Various Quaternary Ammonium Compounds

It was found that polyquaternium-4 largely contributed to providing smoothness to the hair. It also made the application of the product easy and plush. When polyquaternium-4 is employed, the formula glided through the length of the hair and completely coated it to the end. This efficient film forming also helped in a uniform distribution of the product throughout the head. In comparison, the use of polyquaternium-11 (polymeric quaternary ammo N-Vinyl Pyrrolidone and dimethyl aminoethylmethacrylate) changed the viscosity of the product and the performance of the product because it felt "heavy" on the hair (weighed the hair down) and the use of Polyquaternium-7 (polymeric quaternary ammonium salt of Acrylamide and Diallyldimethyl Ammonium Chloride) made the hair appear less hydrated or moisturized (looked dry).

From all the studies and experiments illustrated above, it was concluded that the combination of guar, cationic guar, acrylates-based polymer, and cationic cellulosic quaternary ammonium compound would give the optimum performance.

| Attributes/ Materials | GUAR | CATIONIC GUAR | ACRYLATES- BASED POLYMER | CATIONIC CELLULOSIC QUATERNARY AMMONIUM COMPOUND | COMBINATION OF ALL 4 INGREDIENTS (FORMULA A) |
|---|---|---|---|---|---|
| MOISTURE | ✓ | x | x | x | ✓ |
| HIGH HOLD | x | x | ✓ | x | ✓ |
| SMOOTH | x | x | x | ✓ | ✓ |
| FRIZZ CONTROL | x | ✓ | x | x | ✓ |

Example VI Comparative Testing

A. Comparative Test

The invention Formula B from Table 1 was tested by stylists against comparative Formula E from Table 1. Formula E contains only one gum, hydroxypropyl guar gum. The two formulas were tested on the hair of 2 models (volunteers).

Formula E had a higher amount of residue on the hair.

Formula B dried faster, maintained better shape memory, felt smoother, was more moisturized, appeared to have slightly more volume, had more body, provided a more densifying effect, was more lightweight, had slightly more root-lift, was more individualized, provided better split end seal, provided better curl definition, had slightly better frizz control, slightly better static and fly-away control, appeared to have higher shine, was softer and more supple with slight positive crunch.

B. Comparative Test

The invention Formula A in Table 1 was tested by stylists against comparative Formula F from Table 1. Formula F is a gel that uses a combination of guar and xanthan gum. The two formulas were tested on the hair of 2 models. It was observed that the invention formula provided better shape and hold while still leaving the hair bouncy and soft. On the other hand, the comparative formula did not provide as much hold or control. In addition to this, the invention formula also provided frizz control and reduction in flaking residue.

C. Comparative Test

The invention formula A was also tested against another comparative formula, Formula G in Table 1. Formula G contained a combination of Acacia Senegal gum, dehydroxanthan gum and guar. It is in the gel category and claims to have good hold.

The test formulas were applied on the hair on the head of human volunteers in a half head study. It was observed that Formula G had great hold but it was found to deposit a coating that felt hard and crunchy on the hair. On the other hand, the invention formula provided hold, flexibility, and smoothness, as well as better shaping properties, i.e., one can move the hair around while still maintain the curl definition.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counterion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

The term "lasting" or "long lasting" or "durable" as used herein means that the cosmetic attribute or effect was observed up to about 30 minutes or up to about one hour or up to about two hours, or up to about three hours or up to about four hours or up to about five hours or up to about six hours or up to about seven hours or up to about eight hours or up to about 12 hours or after an overnight period from the time the composition of the present disclosure was applied to hair on the head of a person.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

The term "substantially free" or "essentially free" as used herein may also mean that the specific material is not added to the composition but may still be present in a raw material that is included in the composition.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair cosmetic composition comprising:
    (a) about 0.1 to about 8 wt. % of hydroxypropyl guar;
    (b) about 0.1 to about 1.8 wt. % of hydroxypropyl guar hydroxypropyltrimonium chloride;
    (c) 0.1 to about 4 wt. % of a copolymer of hydroxyethyl cellulose and of diallyldimethylammonium chloride;
    (d) about 0.5 to about 8 wt. % of at least one polymer selected from VP/dimethylamino ethylmethacrylate copolymer, VP/VA copolymer, and a mixture thereof;
    (e) at least 0.5 wt. % to 8 wt. % of at least one polyol chosen from ethylene glycol, propylene glycol, butylene glycol, hexylene glycol, pentylene glycol, diethylene glycol, dipropylene glycol, 1,3 propanediol, polyethylene glycols, caprylyl glycol, diglycerin, glycerin, and a mixture thereof; and
    (f) water;
    wherein (b) and (a) are in a weight ratio from about 0.1 to about 0.5 ((b)/(a)) and all weight percentages are based on a total weight of the composition.

2. The composition of claim 1, wherein the composition is not an emulsion.

3. The composition of claim 1, wherein the composition comprises less than wt. % of a non-ester oil.

4. The composition of claim 1, wherein the composition comprises less than 1 wt. % of oils.

5. A leave-on hair cosmetic composition comprising:
    (a) about 1 to about 4 wt. % of hydroxypropyl guar;
    (b) about 0.1 to about 1.8 wt. % of hydroxypropyl guar hydroxypropyltrimonium chloride;
    (c) 0.1 to about 4 wt. % of polylquaternium-4;
    (d) about 1.2 to about 4 wt. % of at least one polymer selected from VP/dimethylamino ethylmethacrylate copolymer, VP/VA copolymer, and a mixture thereof;
    (e) at least 0.5 to about 10 wt. % of at least one polyol chosen from ethylene glycol, propylene glycol, butylene glycol, hexylene glycol, pentylene glycol, diethylene glycol, dipropylene glycol, 1,3 propanediol, polyethylene glycols, caprylyl glycol, diglycerin, glycerin, and a mixture thereof; and
    (f) about 70 to about 95 wt. % of water;
    wherein (b) and (a) are in a weight ratio from about 0.1 to about 0.5 ((b)/(a)) and all weight percentages are based on a total weight of the composition.

6. The composition of claim 5, wherein the weight ratio is from about 0.12 to about 0.3.

7. The composition of claim 5 comprising about 1.2 to about 4 wt. % of the VP/dimethylamino ethylmethacrylate copolymer.

8. The composition of claim 5 comprising about 1.2 to about 4 wt. % of the VP/VA copolymer.

9. The composition of claim 5, wherein the composition is not an emulsion.

10. The composition of claim 5, wherein the composition comprises less than wt. % of a non-ester oil.

11. A composition consisting of:
  (a) about 1 to about 4 wt. % of hydroxypropyl guar;
  (b) about 0.1 to about 1.8 wt. % of hydroxypropyl guar hydroxypropyltrimonium chloride;
  (c) 0.1 to about 4 wt. % of polylquaternium-4;
  (d) about 1.2 to about 4 wt. % of at least one polymer selected from VP/dimethylamino ethylmethacrylate copolymer, VP/VA copolymer, and a mixture thereof;
  (e) at least 0.5 to about 10 wt. % of at least one polyol chosen from ethylene glycol, propylene glycol, butylene glycol, hexylene glycol, pentylene glycol, diethylene glycol, dipropylene glycol, 1,3 propanediol, polyethylene glycols, caprylyl glycol, diglycerin, glycerin, and a mixture thereof;
  (f) about 70 to about 95 wt. % of water;
  (g) less than 5.3 wt. % of additives, preservatives, organic solvents, and mixtures thereof;
    wherein (b) and (a) are in a weight ratio from about 0.1 to about 0.5 ((b)/(a)) and all weight percentages are based on a total weight of the composition.

12. A method of treating hair, the method comprising applying the composition of claim 1 to hair.

13. A method for treating hair comprising applying the composition of claim 5 to the hair, and without rinsing the composition from the hair, styling the hair.

14. A method for treating hair comprising applying the composition of claim 11 to the hair, and without rinsing the composition from the hair, styling the hair.

* * * * *